United States Patent [19]

Karlhuber et al.

[11] Patent Number: 4,810,776
[45] Date of Patent: Mar. 7, 1989

[54] PROCESS FOR PRODUCING EPOXY RESIN HAVING A LOW-EHC-CONTENT FROM CHLORINE-SUBSTITUTED CRUDE EPOXY RESIN OF HIGH EHC-CONTENT AND APPARATUS FOR AUTOMATICALLY CONTROLLING SUCH PROCESS

[75] Inventors: Bernhard Karlhuber, Basel; André Fiaux, Ollon; Thierry Schaffhauser, Vessy, all of Switzerland

[73] Assignee: Ciba-Geigy Corporation, Ardsley, N.Y.

[21] Appl. No.: 70,742

[22] Filed: Jul. 6, 1987

[30] Foreign Application Priority Data

Jul. 14, 1986 [CH] Switzerland .......................... 2815/86

[51] Int. Cl.$^4$ .............................................. C08G 59/14
[52] U.S. Cl. ..................................... 528/488; 528/489; 528/492; 549/517; 526/60; 525/507; 525/523; 436/55
[58] Field of Search ....................... 528/488, 489, 492; 549/517; 526/60; 525/507, 523

[56] References Cited

U.S. PATENT DOCUMENTS

| 4,447,598 | 5/1984 | Caskey et al. .................. 528/489 |
| 4,535,150 | 8/1985 | Hunter .............................. 528/489 |

FOREIGN PATENT DOCUMENTS

185622 6/1986 European Pat. Off. .
2233054 1/1975 Fed. Rep. of Germany .
55-104748 8/1980 Japan .
59-44646 3/1984 Japan .

Primary Examiner—John Kight
Assistant Examiner—Frederick Krass
Attorney, Agent, or Firm—Harry Falber

[57] ABSTRACT

In a process for producing epoxy resin with low EHC-content there is added to a continuous flow of the chlorine-substituted starting material continuously, with all reaction parameters constant, a dehydrochlorinizing agent, e.g. NaOH, in an amount approximately the stoichiometrical equivalent of the predetermined EHC-content of the starting material. Ionically bound chlorine is removed from the epoxy resin. A stream of a bypassing portion of the epoxy resin is subjected continuously, with brief periodical interruptions, directly after removal of the ionically bound chlorine, to fluorescence-exciting X-ray irradiation and the total chlorine fluorescence is detected, thereby automatically continuously determining the total chlorine content. All fluctuations of the total chlorine content in the bypassing epoxy resin portion are registered, and the amount of dehydrochlorinizing agent added to the flow of starting material as above—is continuously automatically adjusted to be commensurate with the fluctuations of the total chlorine content registered by X-ray fluorescence.

11 Claims, 6 Drawing Sheets

PROCESS FOR PRODUCING EPOXY RESIN HAVING A LOW-EHC-CONTENT FROM CHLORINE-SUBSTITUTED CRUDE EPOXY RESIN OF HIGH EHC-CONTENT AND APPARATUS FOR AUTOMATICALLY CONTROLLING SUCH PROCESS

BACKGROUND OF THE INVENTION

This invention relates to a continuous process for producing epoxy resin having a low content of easily hydrolyzable non-ionically bound chlorine (EHC) from chlorine-substituted epoxy resin obtained by epoxidation and polymerization from epoxy resin-forming chlorine-substituted starting material. In other aspects, the invention relates to apparatus for automatically controlling such novel process, and a novel measuring cell for use therein.

In the known process for the production of epoxy resins, the final products of the epoxidation and polymerisation usually have a content of EHC which is so high that it imparts to the resin an undesirable electrical conductivity. This is particularly disadvantageous when the epoxy resin is to be used in anti-corrosion coatings, e.g. as cataphoresis resins, or in the electrical and the electronic field. More particularly, electrical conductivity is practically unacceptable in boards for printed circuits, where it would severely reduce the range of applicability of epoxy resin as board material.

The crude resin which is obtained as a principal product in the production of epoxy resin contains about 0.2 to 1.5% by weight of EHC. The EHC-content consists preponderantly of 1,2-chlorhydrines of the formula in which R is an aliphatic or preferably an aromatic radical. The crude resin also contains certain amounts of unsaponifiable chlorine and ionic chlorine, i.e. chloride anions in a crystal lattice.

The term "chlorine" in this description and in the appended claims always means chlorine chemically bound in some manner and never chlorine gas.

The term "unsaponifiable chlorine" is used hereinafter and in the appended claims to mean chlorine atoms bound in an organic aromatic or aliphatic compound, in a manner such that they will not be saponified or "hydrolyzed" by the dehydrochlorinating agents and under the reaction conditions which are conventional in the production of epoxy resins. An example of unsaponifiable bound chlorine is shown in the following formula wherein R represents a preferably aromatic organic radical and R' represents preferably lower alkyl or hydrogen.

In order to obtain epoxy resin of lesser EHC-content, i.e., of 0.07% by weight or less, the crude resin is subjected to a dehydrochlorination treatment. Basic agents, in particular alkali metal and earth metal hydroxides such as sodium hydroxide, potassium hydroxide, lithium hydroxide or calcium hydroxide, alkali metal salts of weak acids such as potassium carbonate, potassium hydrogen carbonate, sodium methylate, potassium n-butylate or potassium ter-butylate, or quaternary ammonium hydrogen carbonates of the formula in which R designates a preferably lower alkyl radical, are conventionally used as dehydrochlorinating agents.

By the dehydrochlorination treatment, a certain portion of EHC will be removed from the crude resin with formation of salts such as sodium chloride, potassium chloride, lithium chloride, calcium chloride, quaternary ammonium chloride and the like.

However, the exact dosing of the dehydrochlorinating agent during a continuous treatment is very critical and not easy to achieve.

For, in the equation there prevails an equilibrium which prevents the obtainment of an EHC-free product. Adding an excess of dehydrochlorinating agent (NaOH) leads to the undesirable formation of polymers which will disturb subsequent treatment steps such as evaporation of liquid and filtration of the end product.

Even the smallest excess amount of dehydrochlorinating agent will initiate polymerizing reactions in the resin. Moreover, polymerization products which are thus formed will gradually block lines for the flow of product, and cause failures in the filtering equipment of the plant; moreover, they will also deteriorate the quality of the finally obtained epoxy resin.

Therefore, the rate of adding sodium hydroxide or other dehydrochlorinating agent is very critical and should be strictly and accurately controlled.

Attempts have been made in the past to overcome this drawback by carrying out at frequent intervals, e.g. every 90 to 120 minutes, manual chemical "wet state" analyses to determine the amount of easily hydrolyzable chlorine in the product being continuously fed into the dehydrochlorination treatment. It is a serious drawback of this wet state analysis that numerous samples have to be taken and that a plurality of operations by hand have to be carried out in order to prepare each sample for testing, involving e.g. saponification and titration, so that the entire process becomes cumbersome and requires a great number of personnel.

A more serious drawback is caused by the fact that analysis results are received after a relatively long delay so that an adjustment of the feed rate of dehydrochlorinating agent can take place only rather late after a change in the EHC-content occurred while, in the meantime, a deficiency or excess of dehydrochlorinating agent has had its detrimental effect on the product. Moreover, the results of the above-mentioned method of analysis are relatively inaccurate.

Therefore, in order to avoid as completely as possible the occurrence of polymerization processes during the dehydrochlorinating treatment, a residual EHC-content of about 500 to as much as 700 ppm (0.05 to 0.07% by weight) is still deemed acceptable in epoxy resin produced by the conventional continuous process. Residual EHC-contents of 200 ppm or even less can be attained by the conventional continuous process only with additional costly EHC-removing treatments. In the unsatisfactory conventional batch process which is above all time-consuming and requires an excessive number of personnel, it would indeed be possible to produce epoxy resin having an EHC-content as low as 70 ppm but such resin would not be commercially acceptable, e.g., for electronic circuit boards, because of its high production costs.

Thus, a process for reducing the content of hydrolyzable chlorine in glycidyl compounds described in European patent application Publication No. 185,622 A2 by Ciba-Geigy AG, published on June 25, 1986 requires the use of considerable amounts of cellulose as an extraneous material in the system.

While it is therefore necessary to produce the epoxy resins usable in the electronic field by a continuous process, the product obtained thereby fails quite frequently to meet the specifications imposed by the customer.

OBJECTS AND SUMMARY OF THE INVENTION

It is therefore a principal object of the invention to provide a novel continuous process for producing epoxy resin having a low content of easily hydrolyzable non-ionically bound chlorine (EHC) from the initially described crude epoxy resin of high EHC content as starting material which involves a dehydrochlorination phase that can be automatically controlled so as to afford a very low EHC content in the final product, preferably of not more than 150±50 ppm, optimally below 100 ppm.

It is another object of the invention to provide a process as described and having the same advantages as set forth in the preceding object which process requires moreover relatively simple apparatus means to be carried out in practice.

It is a further object of the invention to provide a process as described and having the advantages demanded by the foregoing objects which is free from the need of introducing large amounts of extraneous material into the process prior to obtaining the final product of low EHC-content.

It is yet another object of the invention to provide a novel apparatus for controlling the aforesaid novel process having the advantages set forth in the preceding objects which apparatus is of satisfacory accuracy in controlling in particular the dehydrochlorinating phase which accuracy is greater than could be achieved in the prior art processes.

It is therefore a still further object of the invention to provide an apparatus as described and affording the advantages mentioned in the preceding object, which apparatus is adapted for providing a quick response, high sensitivity to fluctuations in the total chlorine content of the reaction mixture and the capability of reproducing results of measurements carried out thereby, thus enabling a satisfactory degree of automatization of the process.

These objects are attained as far as the novel process is concerned by providing, in accordance with the invention, a process of the initially described kind which is automatically controlled during the principal phase thereof and comprises, before starting a continuous operation, the steps of (1) analyzing a sample of the same crude resin obtained by the epoxidation and polymerization of epoxy resin-forming starting material so as to chemically ally bound determine the content of ionically bound chlorine therein (i.e. the concentration of chloride anion); and (2) subjecting a sample of the crude epoxy resin starting material to fluorescence-exciting radioactive irradiation through a solid separating layer transmissive for the radioactive radiation, and detecting the total chlorine fluorescence, thereby measuring the total amount of all (bound) chlorine in the sample, the said chlorine being the sum total of unsaponifiable chlorine, non-ionically, but easily saponifiably bound chlorine (EHC) and ionically bound, i.e., also readily saponifiable chlorine (chloride anion) to the extent that the last-mentioned component has not yet been removed beforehand;

(3) gently saponifying a sample of the said crude epoxy resin starting material and titrating the amount of ionic chlorine formed therein by step (2), together with the content of ionically bound chlorine determined in step (2), not removed before that step, and deducting the detected amount from the total chlorine content, thereby determining the amount of unsaponifiably bound (non-EHC) chlorine therein; and then, during continuous operation over a longer period:

(a) adding continuously flow of chlorine-substituted crude epoxy resin-starting material, while maintaining all reaction parameters substantially constant, a dehydrochlorinating agent in an amount being initially in the range of from the stoichiometrical equivalent to one slightly deviating from such equivalent of that chlorine amount which is the difference between (i) the total amount of all chlorine determined in step (2), and (ii) the sum of the amount of ionically bound chlorine determined in step (3);

(b) removing continuously ionic chlorine from the epoxy resin being formed;

(c) automatically periodically determining, while the reaction continues, the total chlorine content in at least a small bypass portion of the epoxy resin directly after removal of the ionic chlorine therefrom in step (b) in the same manner as in step (a), (d) registering all fluctuations of the total chlorine content in the small bypassing epoxy resin portion, and (e) continuously automatically adjusting the amount of said dehydrochlorinating agent added to the flow of crude resin starting material in step (a) to be commensurate with the fluctuations of the total chlorine content registered in step (b).

The steps (1), (2) and (3) of testing the crude resin starting material must only be carried out when the continuous process is started up for the first time with a fresh batch of crude epoxide resin of high EHC-content obtained from the epoxide-forming starting material in order to determine the contents of the various types of differently bound chlorine in the new batch. As this batch is being consumed in the continuous, automatically controlled dehydrochlorination phase, additional crude resin starting material can be added and it is then not necessary to repeat steps (1) to (3) as any changes in the EHC-content in the epoxy resin being formed will be detected immediately at the end of the dehydrochlorination phase as shall now be explained more in detail.

Of course, if the process-type is changed after a first run is over, e.g. from a Taffy-type to an Advancement method or viceversa, the steps (1), (2) and (3) must be repeated. The type of process used must not and, of course, would not normally be changed during a continuous dehydrochlorination phase.

The control of the continuous phase in the process of the invention comprises steps (a), (b) and (c) and is based on our discovery that, when maintaining the process parameters, namely, the temperature, the flow rate, the stirring speed and range, the pressure and the composition of the reaction mixture constant throughout the continuous phase, then the content of unsaponifiable chlorine and the content of ionically bound chlorine both will remain constant. Consequently, fluctuations in the total content of chlorine during the continuous phase are due to and representative of fluctuations in the EHC-content, i.e., the content of hydrolyzable, non-ionically bound chlorine in the flow of reaction mixture during dehydrohalogenization phase.

Consequently, detected fluctuations during the continuous control of the total content of chemically bound chlorine in the epoxy resin formed, and immediately at the end of the dehydrochlorination phase, will represent accurately fluctuations of the EHC-content and signals detected by a detector unit of the X-ray fluorescence analyzer in the control apparatus according to the invention can be used not only for registering continuously the EHC-content of the epoxy resin immediately after it has been produced, but can also be transmitted continuously to the control of the feed pump for dehydrochlorinizing agent, e.g. sodium hydroyide, thus adjusting the feed rate of this agent to the reaction mixture and thereby rendering the process fully automatic.

For example, from the data of, e.g. 1300 ppm of unsaponifiable chlorine and 2 ppm of ionically bound chlorine in a starting batch having a total chlorine content of 1800 ppm, a content of 498 ppm EHC is initially determined. A change in the EHC-content, e.g. to 518 ppm, will thus result in a change of the total chlorine content to 1820 ppm. On the basis of this change of the total chlorine content, the amount of, e.g., sodium hydroxide being fed into the process will be promptly increased by the amount stoichiometrically equivalent with the increase by 20 ppm of the total chlorine content. It will thus be possible to continuously adjust the feed rate of the dehydrochlorinating agent with an accuracy of about 10 to 15 ppm.

Measuring the total chlorine content is carried out by means of a measuring cell in the control apparatus according to the invention during a determined measuring period which is normally shorter than the continuous dehydrochlorination phase in the process according to the invention required for processing an available batch of epoxy resin-forming starting material.

Such measuring period lasts preferably 3 to 5 and not more than 10 minutes, the measuring cell should then be rinsed, preferably, for about 2 minutes, whereupon measuring of the total chlorine content in the epoxy resin being formed is resumed.

Assuming that it would take a run of about one hour through the dehydrohalogenizing phase to use up an initially available batch of the starting material, this means that about five to twelve measuring periods and intervening rinsing periods would cover the entire length of time of the continuous phase. This should suffice to provide adequate control of the entire phase and ensure production of an epoxy resin with satisfactorily low EHC-content. In actual practice, the continuous phase of the process may run for a full six 24-hour days or longer.

In order to achieve the briefest possible sojourn time of the epoxy resin in the measuring cell, the resin should be passed through the cell under excess pressure, preferably of at least one bar.

The separating layer through which irradiation of the epoxy resin passing through the measuring cell takes place is preferably a thin window of suitable material to be described more in detail further below.

The control apparatus according to the invention comprises besides the above-mentioned measuring cell and a source of radioactive radiation such as an X-ray or radionucleide source, a detecting device which measures the total chlorine fluorescence and transmits the resulting signal as dosing parameter to a control unit of the pump means feeding continuously dehydrochlorinizing agent into the reaction flow. By "radioactive" we mean non-corpuscular radiation.

After each measuring period there is preferably interposed a rinsing period, of preferably not less then 2 minutes, during which the measuring cell is rinsed with a rinsing agent such as methyl-isobutyl-ketone, toluene, acetone, methanol or isopropanol.

It is recommended that after one or preferably after several measuring periods the measuring cell be recalibrated, in a manner to be described further below, using as calibrating fluid preferably methylisobutylketone or isopropanol which is doped with a chlorine-containing substance, soluble in the respective solvent, in two different concentrations one of which may be zero.

In order to maintain a sufficient viscosity of the epoxy resin being passed through the measuring cell in the apparatus according to the invention, it is preferred to provide a heating device by means of which the temperature of the cell can be held at least at 65° C. or higher.

Crude epoxy resin starting materials suitable for use in the process according to the invention are, for instance, crude bisphenol-A diglycidyl ether, bisphenol-F diglycidyl ether, tetrabromobisphenol-A diglycidyl ether, epoxy-phenol novolak, epoxy-cresol novolak, solid bisphenol-A epoxy resin, bisphenol-F epoxy resin, an epoxy special resin such as butanediol diglycidyl ether, hexahydrophthalic diglycidyl ester, 1,3-bis-(4-glycidyloxybenzal)-acetone or hydantoin triglycide.

Suitable dehydrochlorinating agents for use in the process according to the invention have been listed further above.

It is known to measure the concentration, for example, of chemically bound chlorine with the aid of X-ray fluorescence analysis (see German Offenlegungsschrift No. 2,233,054 of Gesellschaft für Kernforschung mbH, D-7500 Karlsruhe, published on 17 Jan. 1974).

The apparatus described in this publication uses a window interposed between the sample a radionucleide source, e.g. the isotope Fe-55. A metallized synthetic resin foil is used as the window.

A non-dispersion type fluorescence X-ray analyzing device such as described by Hideo Satou in Japanese patent application No. 55-104,748(A), published on Oct. 31, 1980 in Patents Abstracts of Japan, Vol. 4, No. 156, (P-34) (638) comprises a vacuum X-ray chamber having a measuring window of beryllium on which a sample to be tested must be placed.

A method of detecting the chlorine content in an epoxy resin is particularly described by Momoko Takemura in Japanese patent application No. 59-

44646(A), published on July 10, 1984 in Patent Abstracts of Japan, Vol. 8, No. 147 (P-285) (1584). A germanium single crystal is used for separating out the intrinsic X-ray of chlorine (C/K$_\alpha$-line).

Another method and apparatus which employs energy-dispersive X-ray fluorescence using a radionucleide source for excitation in application for on-stream analysis is described by Dieter K. Donhoffer in "Atomkernenergie/Kerntechnik" Vol. 44, No. 4 of June 1984, pages 266–268 (D-8000 München). In measuring the chlorine content of oligomers in an On-Stream measuring system of the ELBEST type, Donhoffer found in necessary to rinse the space between the sample surface and a counter tube in the apparatus with nitrogen in order to overcome the disturbing effect of argon present in the air.

The use of X-ray fluorescence analysis of the total bound-chlorine content for the continuous control of the dehydrochlorination phase in the process of producing epoxy resin according to the invention did, however, pose a number of problems that had to be solved by us before obtaining useful data adapted for the control of the continuous feed of dehydrochlorinating agent in the reaction phase of steps (a) to (c).

The first serious problem encountered by us was caused by the tendency of the resin being subjected to X-ray fluorescence to polymerize, which results in layers of polymerizate being deposited on the measuring window of the control apparatus and adulterating the measured results.

The second serious problem arose from the choice of window material for the measuring window in the X-ray fluorescence analyzer. The window material must not absorb the fluorescence signal too strongly. Moreover it must be able to withstand, besides the depression or suction effect of the vacuum being applied, the excess pressure of the resin flowing past the cell. A vacuum must be applied to the apparatus chamber because air filling the entire interior of the apparatus chamber, enclosing the cell, an X-ray tube and the detecting unit and thus being present in the interspace between the detecting unit and the sample on the measuring window, would disturb the fluorescence signal; for, a spectral line of argon is so close to that of chlorine in the fluorescence spectrum that disturbing interferences between them could not be avoided. The excess pressure exerted by the flowing resin, as mentioned hereinbefore, is preferably held at least at one bar in order to shorten as much as possible the sojourn time of the resin in the measuring apparatus.

Moreover, the window material must be resistant to corrosion by the resin as well as to the various substances passed over the window during measuring, rinsing and calibrating operations. Of course, the window material must be resistant to the continuous irradiation from an X-ray or radionucleide source.

Therefore, a control apparatus for measuring the total chlorine content in the epoxy resin produced in the dehydrochlorination phase of the process according to the invention comprises a source of radioactive radiation, a measuring cell having a wall comprising a measuring window, preferably of beryllium, through which window the radiation from the said source is directed, flow line means connected to the measuring cell and adapted for passing a stream of epoxy resin in a liquid state through the measuring cell, and a detecting unit for measuring the fluorescence excited by the radioactive radiation in the chlorine atoms present in the epoxy resin passing through the cell.

The term "radioactive radiation" as used in this application comprises X-rays adapted for exciting the chlorine in the epoxy resin to emit fluorescence.

The radiation source can be an X-ray tube or a radionucleide.

The detecting unit preferably comprises a monochromator and proportional counter. It can also comprise a semiconductor as detector.

The beryllium window of the measuring cell has a thickness of preferably 0.05 to 0.5 mm, optimally of 0.1 mm.

BRIEF DESCRIPTION OF THE DRAWINGS

Further objects and advantages of the process and apparatus according to the invention will become apparent from the following more detailed description thereof in connection with the accompanying drawings in which.

DETAILED DESCRIPTION OF THE EMBODIMENTS SHOWN IN THE DRAWINGS

Figure 1:
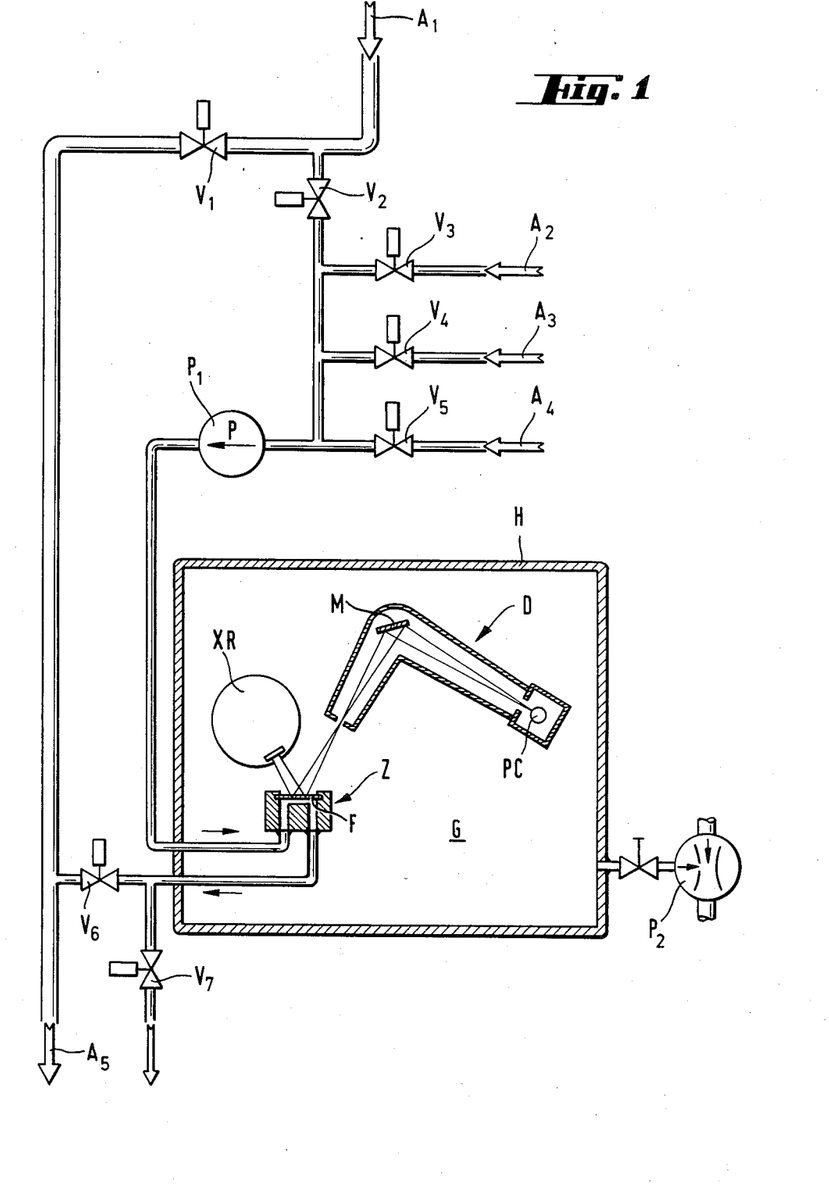
FIG. 1 shows schematically a control system for use in the process according to the invention.

In the schematic representation of a control system shown in FIG. 1, the arrow $A_1$ indicates the entry port and the arrow $A_5$ the exit port of a bypass line, branched off from the main line $A_1$-$V_1$-$A_5$, conveying a crude epoxy resin in a flowable state or a solution of epoxy resin a small amount of which whose total chlorine content is to be measured, being directed by the bypass line into a measuring device contained in the housing H. The measuring ddevice comprises the measuring cell Z, an X-ray tube XR and a detecting unit D.

The main line from the entry port $A_1$ to the exit port $A_5$ is controlled by a bypass valve $V_1$.

A branch line from the entry port 1 to the exit port 5 is controlled by a valve $V_2$ from where it passes through a feed pump $P_1$ to the measuring cell Z and through the latter and out of the casing H back into the bypass line via an open valve $V_6$, while the valve $V_7$ controlling a recycling line is closed.

The housing H is connected to a vacuum pump $P_2$ by means of which the housing interior G can be evacuated.

When the valve $V_2$ is opened and the open cross-sectional area of the valve $V_1$ is sufficiently reduced, epoxy resin from the entry port $A_1$ will be pumped into the branch line and, with valves $V_3$, $V_4$ and $V_5$ being closed, the epoxy resin will be pumped by the pump $P_1$ with a desired pressure of at least one bar above normal into the measuring cell Z and will be returned to the bypass line as long as the valve $V_6$ in the branch line is open and the valve $V_7$ is closed.

In the measuring cell Z the resin is caused to flow past the inside face of a window F through which it will be excited by irradiation with X-rays from the X-ray tube XR which is lodged outside the measuring cell Z. The fluorescence rays typical for chlorine are taken up selectively and quantitatively by the detector unit D. The cell Z is provided with a heating unit (not shown) to keep its temperature above 65° C. The housing H has lead-plated interior walls as protective shielding of the radiation source.

Conventional devices for controlling the temperature and the pressure prevailing in the cell channel for the resin to be tested are likewise provided, but have been omitted from FIG. 1 for the sake of clarity.

Instead of the X-ray tube XR, a radio nucleide can be used; however, the use of an X-ray tube is preferred because it causes a stronger chlorine fluorescence, which is weak per se, than a radio nucleide such as Fe-55 would.

A proportional counter PC is preferred in the detector unit D which also comprises as a monochromator M, for instance, a germanium single crystal.

When using a semiconductor detector in lieu of the proportional counter PC, the monochromator M can be omitted. However, the semiconductor detector will have to be cooled continuously with liquid air in order to attain a sufficient resolution given the low energy (only 2.6 keV) of the $C/K_\alpha$ line of chlorine.

The fluorescence X-ray analyzing device constituted by the detector unit can be of the dispersion type or the nondispersion type. We have obtained best results with a wave length dispersive type of analyzer.

The measuring device shown in FIG. 1 is connected with a conventional evaluation unit (production computer; not shown) in which the known contents of unsaponifiable chlorine and ionically bound chlorine, which have been previously determined in steps (1) to (3) supra, are deducted from the total chlorine content being determined continuously by the measuring device, thus affording continuously signals of the content of EHC which are to be available as signals for controlling and adjusting continuously the feed of dehydrochlorinating agent into the process.

In order to maintain the amounts of unsaponifiably bound chlorine and ionically bound chlorine (chloride anions) in the epoxy resin being produced truly constant with a sufficient degree of accuracy, it is necessary to maintain constant the composition and quality (purity) of the starting material, e.g. epichlorohydrin or bisphenol-A, the type of process, and the above-mentioned reaction parameters such as temperature and reaction time.

The measuring signal is constituted by individual pulses which are each generated by a photon impinging on the detector. These pulses are statistically distributed. In order to equalize the fluctuations resulting therefrom, the pulses must be accumulated during a certain length of time. This can be effected, for instance, by a computer on a digital base. The measuring accuracy is proportional with the square root of the number of accumulated pulses, i.e. it increases with the square root extracted from the accumulating time. The measuring signal is thus available discontinuously.

Alternatively, the pulses can be converted to a voltage by means of a frequency-voltage converter. The rapid statistical fluctuations of this voltage can subsequently be smoothed by means of a low pass filter whereby a continuous measuring signal is obtained.

As has been mentioned hereinbefore, radioactive radiation will generate free radicals which will initiate polymerization effects in epoxy resins. The following steps will help in limiting the occurrence of such undesirable polymerizations.

As a first preventive step, the pressure, and thereby the flow rate, of the resin flowing through the measuring cell Z will be increased by means of speeding up the pump $P_1$, whereby the sojourn time of the resin in the measuring cell is strongly reduced. An excess pressure of one bar has been found to be sufficient in practice to achieve this end.

As a second preventive step, the measuring cell Z is of such design that the flow of epoxy resin through the same will remain laminar even at increased pressure and that there will be no blind angles in the flowpath of the resin inside the cell. A preferred design of the cell shall be described further below.

The two above-mentioned preventive steps are, however, not sufficient to avoid completely the occurrence of polymerizations in the resin passing through the cell Z. Therefore, there will occur some deposits of polymerizate on the walls of the cell Z, which are particularly disturbing when they are formed on the measuring window F as they will lead to erroneous fluorescence signals. A layer of polymerizate having only a thickness of 3 to 5 microns deposited on the measuring window will absorb 90% of the fluourescence signal.

Therefore, as a third preventive step, the resin flowpath in the measuring cell is cleaned from time to time by opening the valve $V_1$, closing the valve $V_2$ and opening the valve $V_3$, while keeping valves $V_4$ and $V_5$ closed, opening valve $V_7$ and closing valve $V_6$. Thereby, a stream of rinsing liquid is pumped through the entry port $A_2$ into the system (FIG. 1) by means of the pump $P_1$, passes through the cell Z and, dissolves polymerizate deposits in the flowpath and from the underside of the window F and the waste rinsing liquid, is discharged from the system by way of the valve $V_7$ and can be recycled into the resin-producing process as far as the rinsing agents can be re-used therein. This is the case when methyl-isobutyl ketone, toluene, acetone, methanol or isopropanol are used as such rinsing agents.

In order to ensure the obtainment of optimally accurate measuring results, it is recommended that the measuring device be calibrated from time to time. For this purpose, a rinsing period is followed by two calibrating steps which require closing of the valves $V_2$ and $V_3$ and first opening the valve $V_4$. The pump $P_1$ will then pump a reference solution having a determined chlorine content $[Cl]_1$ from the entry port $A_3$ into the measuring cell Z, and again out of the system through the exit valve $V_7$, whereupon valve $V_4$ is closed and the valve $V_5$ is opened, and another reference solution having a determined chlorine content $[Cl]_2$ will be pumped from the entry port $A_4$ through the cell Z and out of the system by way of the valve $V_7$. Measuring of the chlorine contents of these two reference solutions will afford two different values which can be plotted to establish the straight calibration line in the desired measuring range on which all other chlorine data measured by the cell Z will be found.

Figure 2:
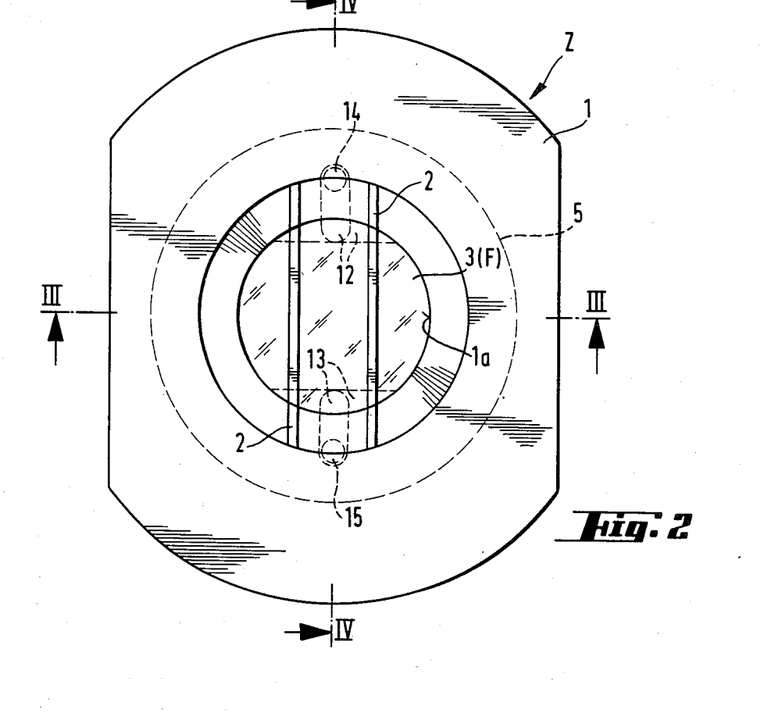
FIG. 2 is a top view of a measuring cell used in the system of FIG. 1.
Figure 3:
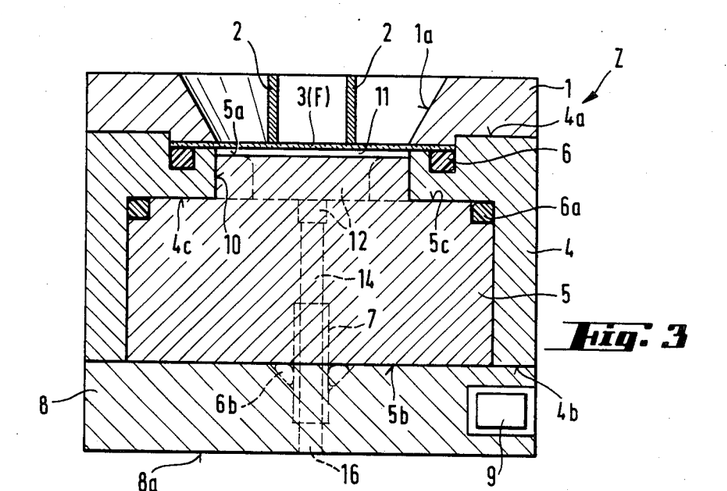
FIG. 3 is a cross-sectional view of the measuring cell taken in a plane indicated by III—III in FIG. 2.
Figure 4:
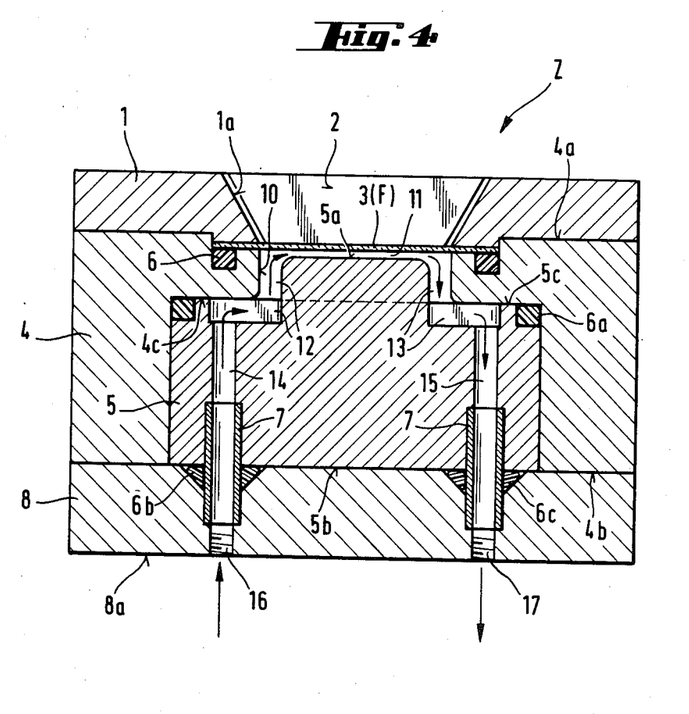
FIG. 4 is another cross-sectional view taken at a right angle relative to the view of FIG. 3 and in a plane indicated by IV—IV in FIG. 2.

In FIGS. 2 to 4 a preferred embodiment of the measuring cell Z is shown on an enlarged scale. The measuring cell comprises a lid 1 having a central opening 1a closed by a window 3 and two parallel reinforcing ledges 2 which extend across the lid opening 1a and stiffen the cell lid 1 against the external underpressure prevailing in the evacuated interior G of the casing H of the measuring device as well as the internal excess pressure of the resin passing on the underside of the measuring window 3. The lid 1 is supported on the peripheral top face 4a of the cell shell 4 having an enlarged cavity opening out of the bottom face 4b of the cell shell 4 and having a central reduced diameter opening 10 in its top face 4a, which is sealed off by the diaphragm window 3 and an O-ring 6 lodged in an annular groove in the top face 4a about the central opening 10.

A guiding core 5 fills the cavity of the cell shell 4 but leaves at its top end a circular space 11 and two channels 13 free between the underside of the window 3 and the internal sidewall of the shell 4 about the opening 10 in the latter on the one hand, and the top face 5a of the guiding core 5 on the other hand.

The cell shell 4 and the guiding core 5 surrounded by the latter are mounted with their bottom faces 4b and 5b on the cell bottom block 8. An O-ring 6a seals an annular upper shoulder 5c of the core 5 against the underside 4c of the annular shoulder about the central opening 10 of the inner cavity end wall in the cell shell 4. Radially extending branches of the channels 12 and 13 extend outwardly below the underside 4c of the shell shoulder mentioned in the form of grooves in the shoulder 5c of the core 5. A heating device 9 is provided in the bottom block 8 (FIG. 3).

The guiding core 5 is provided with two axial ducts 14 and 15 which open out of the shoulder 5c of the core 5 and register with the radially extending branches of the channels 12 and 13 whereby the axial ducts 14 and 15 are in free communication via the channels 12 and 13 with free space 11 at the underside of the window 3. The lower open ends of the ducts 14 and 15 register with axial ducts 16 and 17, respectively, in the bottom block 8 which open out of the bottom face 8a thereof and of which the lower end of duct 16 can be connected to the line for conveying epoxy resin from the pump $P_1$ (FIG. 1) to the cell Z and the lower end of duct 17 can be connected to the line from the cell Z to the exit port $A_5$ or the discharge or recycling line controlled by valves $V_6$ and $V_7$, respectively. (FIG. 1).

When using the cell Z to measure the total chlorine content of epoxy resin, the latter is urged by the pump $P_1$ into the entry duct 16 in the bottom block 8 and upward through the axial core duct 14 and the adjoining channel 12 into the space 11 at the underside of the beryllium window 3. Through the window 3 the flowing resin is subjected to irradiation from the X-ray source XR (FIG. 1) and is urged on through the exit channel 13 into the downward leading core duct 15 and through the exit duct 17 in the cell bottom block 8 and the line connected thereto via the open valve $V_6$ back into the bypass line to the exit port $A_5$ (FIG. 1). The circular free space 11 below the window 3 is preferably relatively narrow so that a large surface of the resin is exposed to the X-rays while the resin passes rapidly through the space 11 into the exit channel 13 and its sojourn time in the space 11 and, indeed, in the entire channel system of the cell Z is only a very brief one. In order to ensure laminar flow of the resin and avoiding turbulence therein caused by dead angles, the rim of the shoulder underside 4c about the central opening 10 is rounded off.

Moreover, the flow of the resin through the ducts 14, 15, 16 and 17 can be smoothed by tubular inserts 7 which bridge the joints between the bottom face 5b of the core 5 and the bottom block 8 and are mounted in corresponding recesses in these elements and being sealed therein by O-rings 6b and 6c, respectively. Owing to its relatively high viscosity at room temperature, the epoxy resin is conveyed through the channel system in the cell Z either at elevated temperature, achieved with the aid of the heating device 9, or in solution. In practice, a heating of the cell to 65° C. has been found satisfactory.

The material of the window 3 is critical for the reasons set forth further above. However, when rinsing or calibrating the measuring device, a Mylar window which is being used conventionally in the art would be quite sufficient if used only once. Beryllium windows proposed in the prior art have the drawback of being corroded by weakly basic or weakly acid water. Nevertheless, we have found that, when used in the process according to the invention directly following the end of the dehydrochlorination phase, i.e., when there is no significant excess of sodium hydroxide or the like agent present in the freshly produced crude epoxy resin, the dehydrochlorinizing agent being slightly underdosified anyway to avoid polymerizations, the beryllium window appears not to be attacked by the crude resin. Moreover, its mechanical strength in the measuring cell has been found to be completely adequate even in longer time use.

Figure 5:
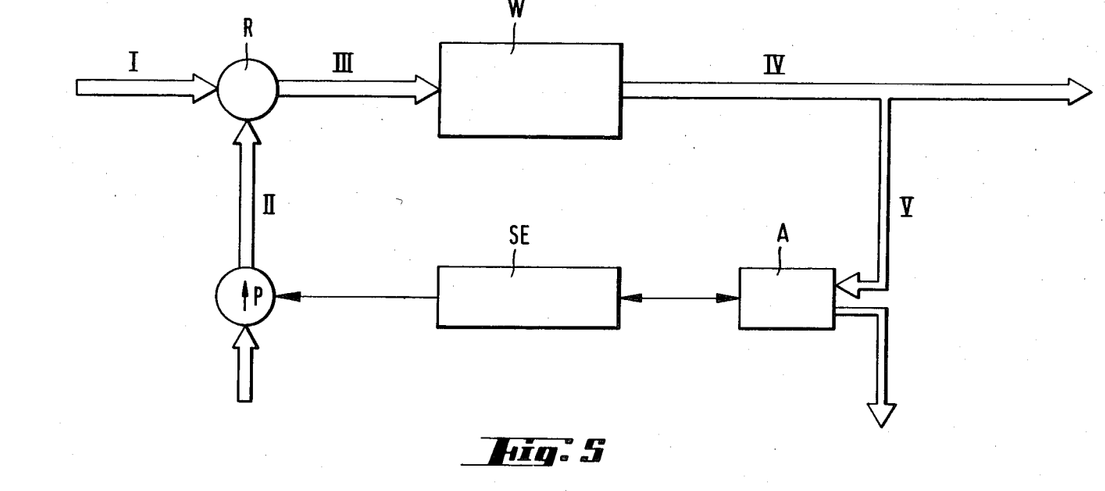
FIG. 5 is a block diagram showing a preferred arrangement of integrating the control system of FIG. 1 in the production process according to the invention.

In the block diagram shown in FIG. 5 the measuring system according to the invention is shown incorporated in a complete production process for epoxy resin. In the reactor R, the crude resin I in a conveyable flowing state or in solution is mixed with the basic agent II and the resulting mixture III is introduced into a washing station W, where the chloride produced in the mixture by reaction of the basic agent with the crude resin is washed out. A portion V of the wet crude resin IV leaving the washing station W is branched off and conveyed into the measuring device A illustrated in FIGS. 1 to 4. The measuring device is connected with a computing unit SE which calculates from the measure signal the content of easily hydrolizable chlorine (EHC) remaining in the resin and derives therefrom a control signal for the dosing pump PN. As the content of EHC in the resin is given in percentages and the addition of sodium hydroxide or the like dehydrochlorinating agent must be in absolute amounts, the flow rate in amounts per hour must be known and must be kept constant very accurately. The information relating to the EHC-content can be indicated additionally directly on a gauge in ppm or can be printed out by a printer (not shown) connected with the computing unit SE.

A particular advantage of the control apparatus and measuring device according to the invention resides in the fact that the signals emitted by the same need not be used solely for the control of feeding sodium hydroxide or the like dehydrochlorinating agent, but may also be used to control and adjust other important process parameters. Thus, diverse educts can be dosified, or the temperature or the pH-value of the reaction mixture can be adjusted. Depending on the intended type of application, the software must be adapted to the corresponding control algorithm.

With the aid of the measuring device according to the invention, it has now become possible to obtain "real time" information about the EHC-content of epoxy resin and to react instantly to any deviations from the desired value thereof. Moreover, personnel can be saved as the frequent manual taking and testing of samples has now become superfluous.

The following examples will illustrate the process according to the invention further and in more detail.

EXAMPLE 1

A crude diglycidylether of bisphenol A or bisphenol F, either as such or in a conventional solution, which contains 3000 ppm of easily hydrolizable chlorine is mixed with an aqueous sodium hydroxide solution containing 50% by weight of NaOH continuously and in stoichiometrically equivalent ratios in a reactor cascade with stirring equipment at a temperature of 105° C. The amount of sodium hydroxide solution is calculated to be such that the final epoxy resin product will contain from 150 to 200 ppm of EHC. Subsequent to this reaction step the epoxy resin or a solution thereof is washed with water to remove from the epoxy resin ionically bound chlorine (chloride anions) formed therein. The total chlorine content of the resulting final product is then determined "semi-continuously", i.e. by digital accumulation of the test signal during 3 minutes, by means of a wave length dispersible X-ray fluorescence analyzer at a temperature of 88° C. Thereafter, the measuring cell of the analyzer is rinsed for 2 minutes with methyl isobutyl ketone. Of course, an analog measurement could likewise be carried out in lieu of a digital one. The measured value is 1430±25 ppm. It is used as dosing parameter for the control of the addition of sodium hydroxide in order to reduce the EHC content from 3000 ppm to 165 ppm in the final product.

EXAMPLE 2

A 40% weight/volume solution of crude diglycidylether of tetrabromobisphenol A, of crude epoxy cresol novolak or of epoxy phenol novolak, in toluene or in methylisobutyl ketone is dosed continuously with aqueous sodium hydroxide solution containing from 5% to 50% by weight of NaOH in a multi-stage reactor with stirring equipment. The amount of sodium hydroxide solution is so calculated that the final epoxy resin product contains from 50 to 200 ppm of EHC.

After this reaction step, the resulting epoxy resin solution is washed in order to remove therefrom all ionically bound chlorine formed in the resin, and the total chlorine content of the washed final product is then determined semicontinuously, with intermittent rinsing every 5 minutes, by means of an X-ray fluorescence analyzer at 85° C. The resulting test value is 1310±25 ppm total chlorine in the resin, which corresponds to a content of EHC of 70 ppm. This test value is used as the dosing parameter for the amount of sodium hydroxide solution or of potassium tert-butylate solution to be added in order to reduce the hydrolyzable chlorine in the product from 1000 ppm to 70 ppm.

EXAMPLE 3

A 60% weight/volume solution, in methyl isobutyl ketone or toluene, of a solid crude bisphenol-A or bisphenol-F epoxy resin containing about 400 ppm of EHC is mixed with aqueous sodium hydroxide solution containing 30% by weight of NaOH in a continuous reactor with stirring. The amount of sodium hydroxide solution is calculated to afford an epoxy resin final product with 30 to 150 ppm of EHC. Subsequent to this reaction step the resulting resin solution is washed with water in order to remove from the same the ionically bound chlorine formed therein; the total chlorine content of the resulting washed product is then determined semi-continuously, during 3 minutes of every 5-minute period, with 2 minutes of intermediate rinsing, in a wavelength dispersive X-ray fluorescence analyzer at 80° C. The measured total chlorine in the epoxy resin product as obtained is 900 ppm. It is used as dosing parameter for the control and adjustment of the rate of sodium hydroxide solution in order to reduce the EHC content in the final product from 400 ppm down to 50 ppm.

EXAMPLE 4

A crude epoxy special resin such as a butanediol glycidyl ether containing about 700 ppm of EHC as well as an aqueous sodium hydroxide solution containing 50% by weight of NaOH are dosed together continuously at a temperature of 100° C. into a cascade reactor with stirring equipment. The amount of sodium hydroxide solution is calculated to be such that the final epoxy resin product will contain less than 100 ppm of EHC. Following this reaction step the resulting resin is washed with water in order to remove therefrom the ionically bound chlorine formed therein. The total chlorine content of the washed product was then determined in the same manner as in the preceding Example 3, but at a temperature of 85° C. The measured total chlorine content is then 2200±30 ppm which corresponds to an EHC-content of 80±30 ppm. This value is used as dosing parameter for the controlled adjustment of the amount of sodium hydroxide being continuously fed into the reaction, in order to reduce the content of easily hydrolyzable chlorine from 700 ppm to 80 ppm in the final product.

EXAMPLE 5

As crude epoxy special resin there is used hexahydrophthalic diglycidyl ester containing about 700 to 1500 ppm of EHC. The treatment of Example 4 is repeated, but instead of sodium hydroxide solution there are used stoichiometrically equivalent amounts of solid potassium carbonate (or of an aqueous potassium carbonate solution), and the ionically bound chlorine is removed by filtration instead of washing.

The total chlorine content of the washed or filtered product is determined to be 6000±40 ppm in the final product, and is used as the dosing parameter for the controlled adjustment of the continuously added amounts of potassium carbonate, in order to reduce the EHC-content of the final product to 150±50 ppm.

EXAMPLE 6

As crude epoxy special resin there is used a 1,3-bis-(4-glycidyloxy-benzal)-acetone which contains about 1500 ppm of EHC. The procedure of Example 4 is repeated but instead of the aqueous sodium hydroxide solution of 50% by weight NaOH-content used in Example 4, such solution having a content of only 30% by weight of NaOH is used. The ionically bound chlorine is removed in the same manner as described in Example 2.

The total chlorine content of the washed epoxy resin is determined to be 2600±40 ppm and serves as dosing parameter for the controlled adjustment of the amounts of the 30%-sodium hydroxide solution being continuously fed into the process so that the EHC-content is reduced to below 100 ppm in the final product.

EXAMPLE 7

As crude epoxy special resin there is used a hydantoin triglycide containing about 2500 ppm of EHC. The procedure of Example 4 is repeated, but instead of sodium hydroxide there is used solid potassium carbonate or an aqueous solution of sodium carbonate, and ionically bound chlorine is removed by filtration instead of washing, when needed.

The determination of the total chlorine in the filtered or washed product afforded a value of 2300±30 ppm, which was used as the dosing parameter for the controlled adjustment of the continuous feeding of potassium carbonate into the process, in order to reduce the EHC-content of the final product to less than 100 ppm.

In the preceding examples there can be used, apart from sodium hydroxide and potassium carbonate, also stoichiometrically equivalent amounts of potassium hydroxide, potassium n-butylate, potassium ter-butylate, potassium hydrogen carbonate, sodium methylate, lithium hydroxide and calcium hydroxide as well as quaternary ammonium hydrogen carbonates of the formula $$R_4N^+HCO_3^-$$

wherein R represents alkyl, in particular lower alkyl preferably of from 1 to 4 carbon atoms.

Figure 6:
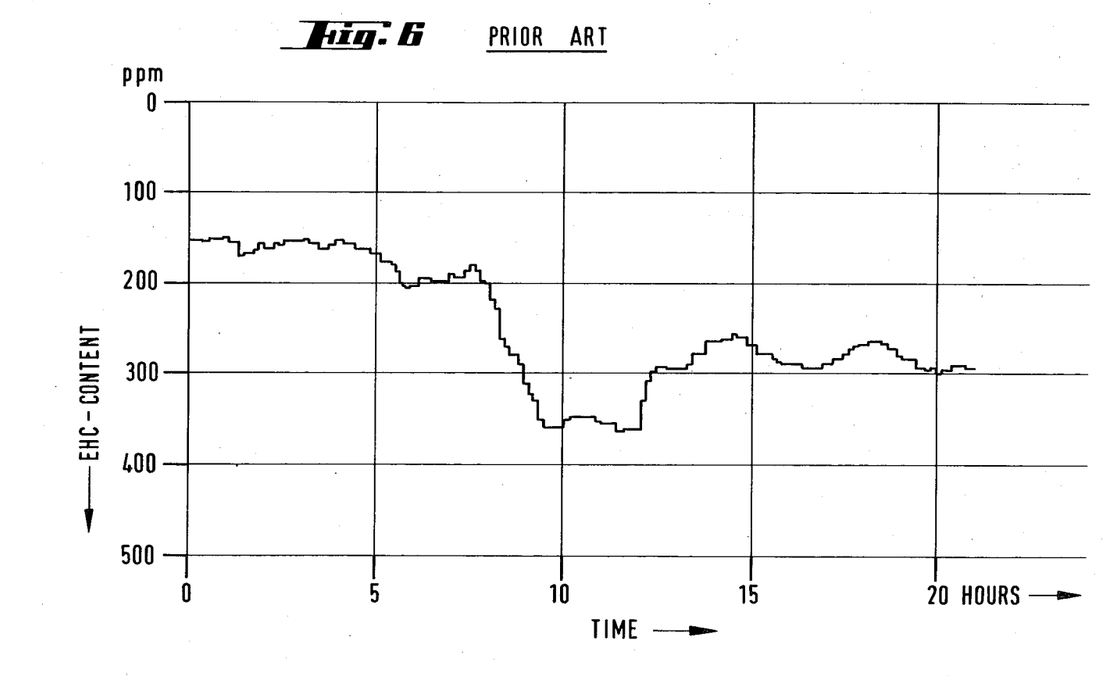
FIG. 6 is a graphic representation of the curve of the EHC content of epoxy resin, with prior art manual control during a period of several hours aiming at the production of an epoxy resin having an EHC content of 150 ppm.

In the diagrammatic representation of FIG. 6 there is plotted on the abscissa the duration (in hours) of a continuous process carried out as described in Example 1, in which the target was an EHC-content of 150 ppm in the final product. The continuous process was controlled with the aid of manually taking probes, analyzing by manual chemical "wet state" analyses, and then adjusting the valve controlling the feeding of sodium hydroxide solution manually.

As seen from FIG. 6, the EHC-contents plotted on the ordinate of the diagram deviated increasingly from the desired EHC-content of 150 ppm, to stabilize somewhat in the range of 300 ppm during the twelfth to twentieth hour of the process.

Figure 7:
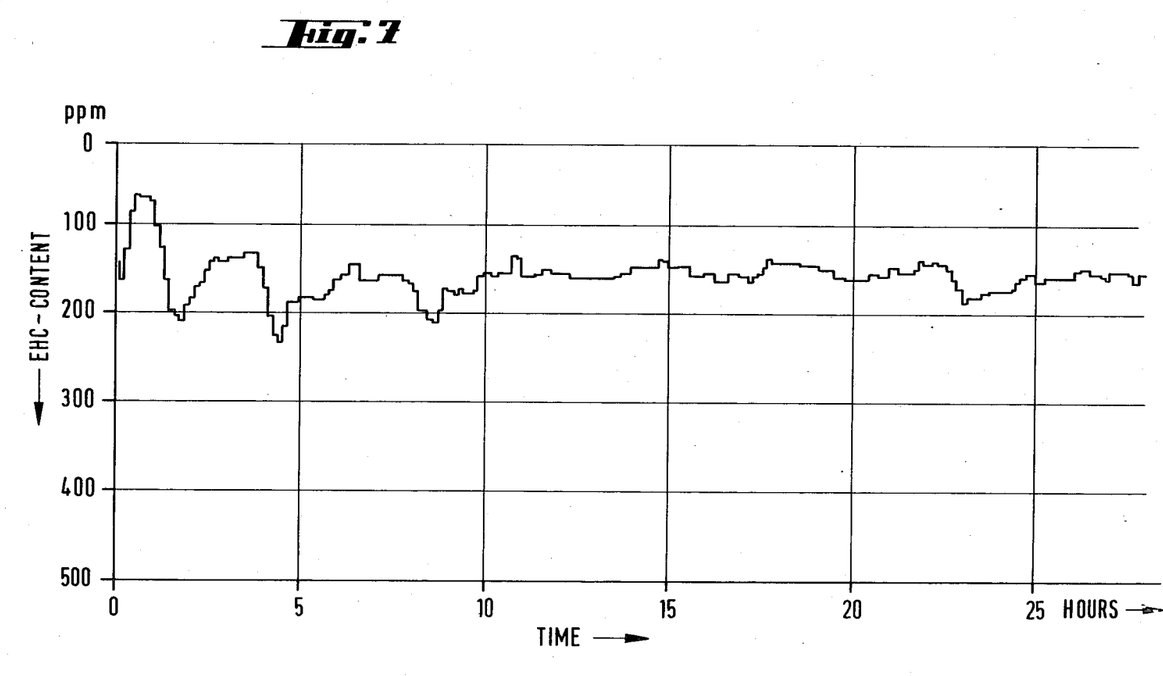
FIG. 7 is a graphic representation of the curve of EHC-content of the same epoxy resin production goal as used in plotting FIG. 6, but controlled in accordance with the process, and with the aid of, the apparatus, according to the invention.

The diagrammatic representation of FIG. 7, plotting process time (in hours) on the abscissa and EHC-contents on the ordinate of the diagram, was established by carrying out exactly the same kind of process as in the case of FIG. 6, but using the control and feed adjusting system according to the invention, with intermediate 2-minute rinsing of the measuring cell as described in Example 1, supra. The diagram of FIG. 7 shows a very satisfactory stabilization of the process after the tenth process hour which lasted for more then fifteen hours thereafter at the desired value of 150 ppm.

We claim:

1. In a process for producing epoxy resin by reacting chlorine-substituted crude epoxy resin of high EHC-content with a basic dehydrochlorinating agent continuously and adjusting the amount of the said agent being admixed with the epoxy resin in a manner such as to decrease the EHC-content of the resin reaction product, the improvement of
   (a) adding continuously to a flow of the crude epoxy resin, while maintaining all reaction parameters of the process constant, an amount of the dehydrochlorinating agent substantially equal to the stoichiometric equivalent thereof required for hydrolyzing the pre-determined EHC-content of the crude epoxy resin;
   (b) removing continuously ionically bound chlorine from the epoxy resin formed in step (a);
   (c) subjecting a flow of at least a small bypassing portion of the epoxy resin, separated from the main stream of the latter, directly after being treated in step (b), in an irradiation zone to fluorescence-exciting radioactive irradiation and detecting the total chlorine fluorescence in said zone, thereby determining continuously and automatically the total chlorine content of the epoxy resin flowing through said zone;
   (d) registering all fluctuations of the total chlorine content in the bypassing epoxy resin portion, and
   (e) continuously automatically adjusting the amount of said dehydrochlorinating agent being added to the crude epoxy resin flow in step (a) to be commensurate with the fluctuations of the total chlorine content registered in step (d);
   whereby the EHC-content of the resulting epoxy resin is reduced to considerably below 200 ppm.

2. The process of claim 1, wherein said small bypassing portion of chloride anion-free epoxy resin is subjected to said irradiation during measuring periods interrupted by rinsing periods, and wherein each measuring period lasts at most 10 minutes.

3. The process of claim 2, wherein each rinsing period lasts at least 2 minutes.

4. The process of claim 2, wherein the stream of bypassing portion of chloride-anion free epoxy resin is interrupted during said rinsing period and replaced by a stream of rinsing agent flowing along the same path as said epoxy resin portion through the irradiation zone.

5. The process of claim 4, wherein said rinsing agent is selected from methyl isobutyl ketone, toluene, acetone, methanol or isopropanol.

6. The process of claim 2, wherein said stream of bypassing epoxy resin portion is maintained at a temperature of at least 65° C. while being irradiated in step (c).

7. The process of claim 2, wherein the bypassing portion of chloride-anion free epoxy resin is under an excess pressure of at least one bar while being irradiated.

8. The process of claim 1, wherein the crude epoxy resin is selected from crude bisphenol-A diglycidyl ether, bisphenol-F diglycidyl ether, tetrabromo-bisphenol-A diglycidyl ether, epoxy phenol novolak, epoxycresol novolak, solid bisphenol-A epoxy resin, solid bisphenol-F epoxy resin, butanediol-diglycidyl ether, hexahydrophthalic acid diglycidyl ester, 1,3-bis-(4-glycidyloxybenzal) acetone or hydantoin triglycide.

9. The process of claim 1, wherein said dehydrochlorinating agent is selected from sodium hydroxide, potassium hydroxide, lithium hydroxide, calcium hydroxide, potassium carbonate, potassium hydrogen carbonate, sodium methylate, potassium n-butylate, potassium-tert-butylate or a quaternary ammonium hydrogen-carbonate of the formula $$[R_4N]^+HCO_3^-$$

wherein $R_4$ represents alkyl.

10. The process of claim 2, wherein, after one of said rinsing periods, two solvent-containing calibrating solutions containing different determined concentrations of chlorine, at least one of which concentrations is greater than zero, are passed successively through the irradiation zone.

11. The process of claim 10, wherein the solvent in said solutions is selected from methyl isobutyl ketone or isopropanol.